United States Patent
Ackerman

(10) Patent No.: US 6,450,963 B1
(45) Date of Patent: Sep. 17, 2002

(54) APPARATUS AND METHOD FOR ULTRASONIC IMAGING OF THE UTERUS AND FALLOPIAN TUBES USING AIR AND SALINE

(75) Inventor: Bernard Ackerman, Metuchen, NJ (US)

(73) Assignee: Ackrad Laboratories, Inc., Cranford, NJ (US)

( * ) Notice: Subject to any disclaimer, the term of this patent is extended or adjusted under 35 U.S.C. 154(b) by 10 days.

(21) Appl. No.: 09/609,050

(22) Filed: Jun. 30, 2000

(51) Int. Cl.⁷ ................................ A61B 8/14
(52) U.S. Cl. .................... 600/459; 600/463; 604/55
(58) Field of Search ................... 600/437, 114, 600/439, 458, 466, 471, 420, 431; 604/48, 55, 96.01, 101.04, 97.02, 102, 104, 515, 82; 128/898; 606/193

(56) References Cited

U.S. PATENT DOCUMENTS

| | | | | |
|---|---|---|---|---|
| 4,466,442 A | * | 8/1984 | Hilmann et al. | 600/431 |
| 5,211,627 A | * | 5/1993 | William | 604/82 |
| 5,242,390 A | * | 9/1993 | Goldrath | 604/55 |
| 5,624,399 A | | 4/1997 | Ackerman | |
| 5,645,561 A | * | 7/1997 | Smith et al. | 606/193 |
| 5,885,216 A | * | 3/1999 | Evans et al. | 600/431 |
| 5,935,098 A | * | 8/1999 | Blaisdell et al. | 604/55 |
| 6,210,330 B1 | * | 4/2001 | Tepper | 600/439 |
| 6,234,958 B1 | * | 5/2001 | Snoke et al. | 600/114 |
| 6,278,892 B1 | * | 8/2001 | Prince | 600/420 |

OTHER PUBLICATIONS

Stern et al.; Comparative Study of Contrast Agents for Hysterosonosalpingography: Air and Water vs. Albunex; *Fertility and Sterility Abstracts*, vol. 70, No. 3, 1998, p. S107.

* cited by examiner

Primary Examiner—Marvin M. Lateef
Assistant Examiner—Ali M. Imam
(74) Attorney, Agent, or Firm—Duane Morris LLP

(57) ABSTRACT

An apparatus for sonographically observing a location and condition of the body. The apparatus has a pump assembly and a catheter assembly fluidly coupled to the pump assembly. The pump assembly includes a first pump for pumping a solution of sterile saline into the catheter assembly and a second pump for pumping micro-filtered air into the catheter assembly. The catheter assembly injects the solution of sterile saline and the sterile saline mixed with micro-filtered air into a location of a body. Further, a method for sonographically observing a location and condition of a body using the above apparatus. The method comprises the steps of inserting the catheter assembly into the location of the body, injecting the solution of sterile saline into the location of the body using the first pump of the pump assembly and the catheter assembly, injecting the micro-filtered air into the saline using the second pump of the pump assembly and the catheter assembly to generate air bubbles in the saline; injecting the saline with the air bubbles generated therein into the location of the body using the first and second pumps of the pump assembly and the catheter assembly; and ultrasonically imaging the location of the body to sonographically observe the location of the body using the bubbles generated in the saline.

21 Claims, 3 Drawing Sheets

APPARATUS AND METHOD FOR ULTRASONIC IMAGING OF THE UTERUS AND FALLOPIAN TUBES USING AIR AND SALINE

FIELD OF THE INVENTION

The present invention relates to an apparatus and method for imaging the anatomical structures of the uterus and fallopian tubes, and more particularly, to an apparatus and method for first injecting a sterile solution of saline into a uterus and its associated fallopian tubes to first observe the condition of the uterus and then generating air bubbles in the saline which are easily seen using an ultrasound scanner to sonographically observe the fallopian tubes.

BACKGROUND OF THE INVENTION

Non-surgical diagnostic procedures for examining the uterus are well known. One such procedure known as hysterosonosalpingography, employs contrast agents and ultrasound imaging techniques for viewing the anatomical structures of the uterus and fallopian tubes. In hysterosonosalpingography, a fine flexible catheter equipped with an inflatable balloon is inserted into the cervical canal and/or into the uterus such that the balloon is positioned in the uterus or cervical canal. Once positioned, an inflation syringe associated with the catheter is used to inflate the balloon with saline to seal and block the cervical canal. A second injection syringe is then used to inject a contrast agent, such as Albunex manufactured by Mallinkrodt Medical, into the uterus, and subsequently into the fallopian tubes.

Albunex and other like contrast agents, are viscous solutions that include surface active agents which generate bubbles when shaken with air prior to injection into the uterus and fallopian tubes. These bubbles can be easily seen using an ultrasound scanner to sonographically observe the fallopian tubes.

Although conventional contrast agents function quite adequately, there are some disadvantages associated with them. One disadvantage is that they are very expensive and difficult for some gynecologists to obtain. Another disadvantage is that conventional contrast agents must be shaken prior to injection, thus making the entire diagnostic procedure cumbersome. A third disadvantage is a very short shelf life.

In response to the cost and unavailability of conventional contrast agents, other contrast mediums have been recently investigated. One such alternative contrast medium is air mixed with sterile solutions of saline. Recent studies indicate that air and saline can be used in place of conventional contrast agents in hysterosonosalpingography, as air and saline have the same contrasting capability as conventional contrast agents.

Unfortunately, conventional methods for generating air bubbles in saline are less than adequate and can be painful. Accordingly, an apparatus and method are needed for injecting a sterile solution of saline into a uterus to sonographically observe same and generating air bubbles in the saline which are easily seen using an ultrasound scanner to sonographically observe the fallopian tubes.

SUMMARY OF THE INVENTION

The invention is directed to an apparatus for sonographically observing a location of bodies, especially the uterus and fallopian tubes. The apparatus comprises a pump assembly and a catheter assembly fluidly coupled to the pump assembly. The pump assembly includes a first pump for pumping a solution of sterile saline into the catheter assembly and a second pump for pumping sterile air into the catheter assembly. The catheter assembly conveys the solution of sterile saline and the saline-air mixture into a location of a body.

The invention is further directed to a method for sonographically observing a location of a body, such as a uterus and its associated fallopian tubes, using the above apparatus. The method comprises the steps of inserting the catheter assembly into the location of the body, injecting the solution of sterile saline into the location of the body using the first pump of the pump assembly and the catheter assembly to observe its condition, injecting the micro-filtered air into the saline using the second pump of the pump assembly and the catheter assembly to generate air bubbles in the saline, injecting the saline with the air bubbles generated therein into the location of the body using the first and second pumps of the pump assembly and the catheter assembly, and ultrasonically imaging the location of the body to sonographically observe the location of the body using the bubbles generated in the saline.

BRIEF DESCRIPTION OF THE DRAWINGS

The advantages, nature, and various additional features of the invention will appear more fully upon consideration of the illustrative embodiments now to be described in detail in connection with accompanying drawings wherein.

It should be understood that the drawings are for purposes of illustrating the concepts of the invention and are not necessarily to scale.

DETAILED DESCRIPTION OF THE INVENTION

The apparatus and method of the invention are especially useful for performing hysterosonosalpingography, which is a non-surgical ultrasound-based diagnostic imaging procedure for examining the anatomical structures of the uterus and fallopian tubes. In the method, a sterile solution of saline is first injected without air to observe uterine pathology. Then, micro-filtered air is added to the saline to observe patency of the fallopian tubes. The apparatus allows the method to be performed rapidly and conveniently, without changing syringes and the infection risks associated therewith.

Of course, one of ordinary skill in the art will recognize that the apparatus and method can also be used in other ultrasound imaging procedures of the body where injection of sterile solutions of saline and sterile air are harmless. For purposes of describing the invention, the term "distal end" is meant to refer to the end furthest from the physician or other person holding the apparatus, and the term "proximal end" is meant to refer to the end closest to the holder of the apparatus.

Figure 1:
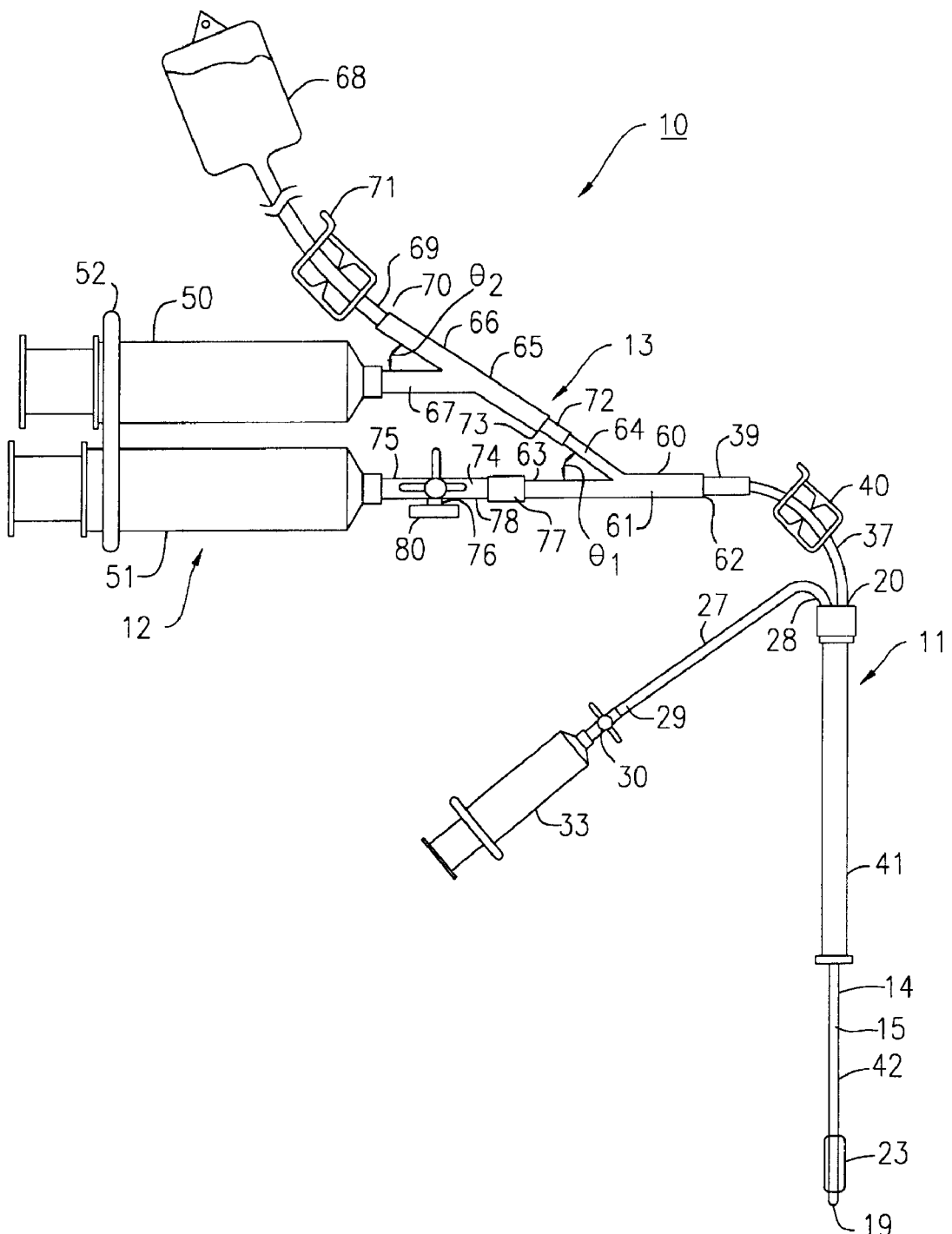
FIG. 1 is an elevational view of an apparatus according to an embodiment of the invention, for injecting a sterile solution of saline into a uterus and its associated fallopian tubes and generating air bubbles in the saline.

FIG. 1 shows an apparatus 10 according to an embodiment of the invention. The apparatus 10 generally comprises a catheter assembly 11 and a pump assembly 12 fluidly coupled to the catheter assembly 11.

Figure 2:
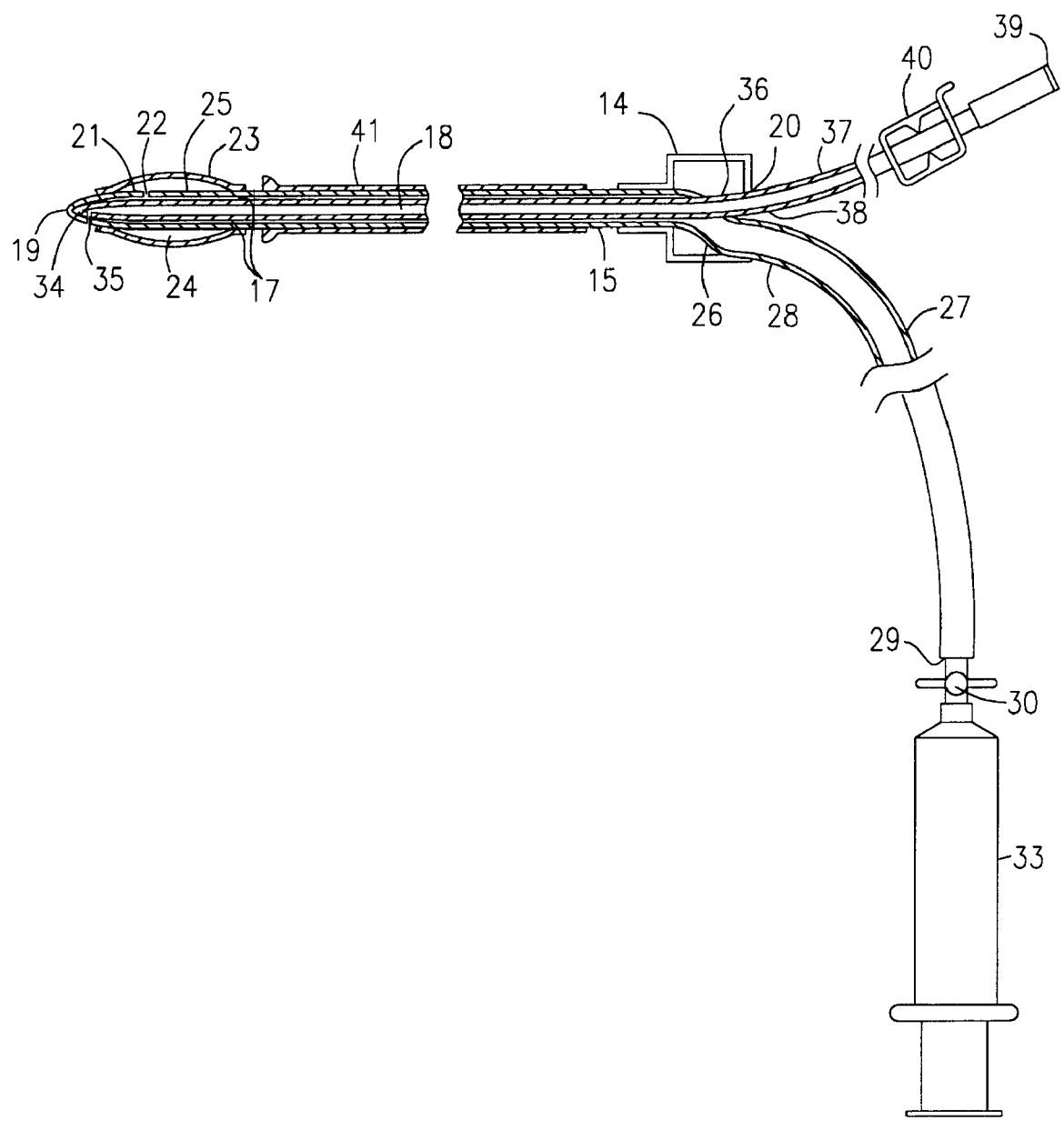
FIG. 2 is a sectional view of the catheter assembly of the apparatus.

As shown collectively in FIGS. 1 and 2, the catheter assembly 11 typically includes a double lumen balloon catheter 14 preferably of the type described in U.S. Pat. No. 5,624,399 issued to Bernard Ackerman, the disclosure of which is incorporated herein by reference. The catheter disclosed therein is primarily intended for non-surgical entry into the uterine cavity, however, one of ordinary skill in the art will recognize its usefulness in other related procedures. This catheter 14 includes an elongated, flexible tubular body 15 having an interior which defines first and second lumens 17, 18. The first lumen 17 extends almost the entire length of the body 15 from the distal end 19 to the proximal end 20 thereof. The marginal distal end 21 of the first lumen communicates Hi via an aperture 22 with the interior 24 of an inflatable intracervical/intrauterine balloon 23 which is mounted around an exterior portion 25 of the catheter body 15. The proximal end 26 of the first lumen 17 communicates with the distal end 28 of a flexible tube-like line 27. The proximal end 29 of the line 27 is coupled to a conventional inline rotary valve 30 and syringe 33. The first lumen 17 cooperates with the syringe 33, valve 30 and line 27 to inflate and deflate the balloon 23.

The second lumen 18 also extends almost the entire length of the body 15 from the distal end 19 to the proximal end 20 thereof. The second lumen 18 has a distal end 34 with a fluid injection aperture 15 and a proximal end 36 that communicates with the distal end 38 of a flexible tube-like fluid line 37, the proximal end 39 of which is removably coupled to a first y-shaped tube element 60 which couples the catheter assembly 11 to the pump assembly 12. Slidably mounted on the fluid line 37 is a conventional lockable plastic pinch clamp 40. The second lumen 18 provides a fluid communication path for the introduction of sterile solutions of saline and micro-filtered air into the uterine cavity and the fallopian tubes.

The catheter body 15 extends through a semi-rigid sheath 41. The sheath 41 can be slidably moved toward the proximal end 20 of the catheter body 15 to uncover a distal portion 42 thereof thereby permitting the same to bend freely, or the sheath 41 can be slidably moved toward the distal end 19 of the catheter body 15 to cover the same to prevent it from bending and flexing in the vagina thus aiding the insertion of the catheter in the cervical canal.

Figure 3:
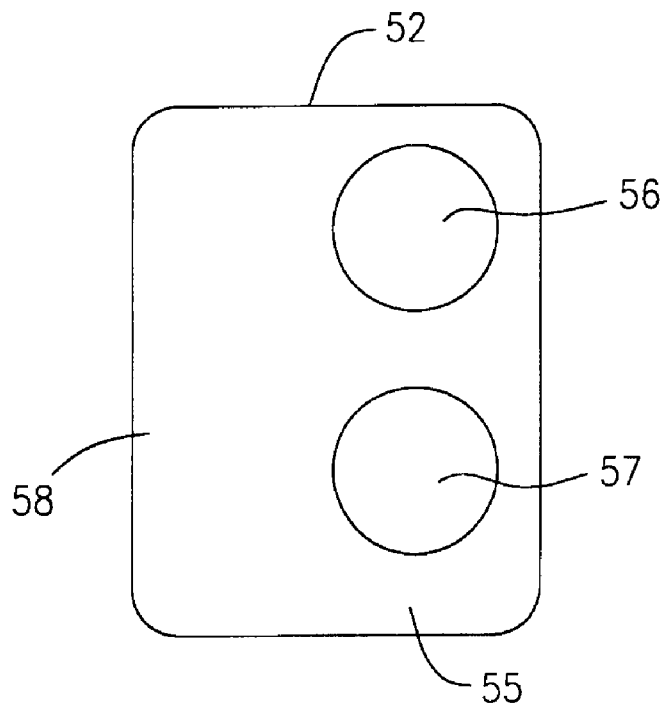
FIG. 3 is an elevational view of the pump holder of the pump assembly of the apparatus.

The pump assembly 12 includes a first pump 50 for pumping sterile solutions of saline or other anachoic fluids (fluids which highlight pathology of the uterus), a second pump 51 for pumping sterile air, and a pump holder 52 which mounts the pumps 50, 51 together as an assembly. In the shown embodiment, the first and second pumps 50, 51 preferably comprise conventional medical-grade syringes. As shown in FIG. 3, the pump holder 52 is typically embodied as a substantially planar member 55 having a pair of apertures 56, 57 which receive the pumps 50, 51 and an extended section 58 that permits a physician or a medical technician to hold the pump assembly 12 and sequentially operate the pumps 50, 51 with a first hand so that the second hand is free to operate an ultrasound scanner (not shown).

A second y-shaped tube element 65 having a main tube 66 and a branch tube 67 splitting off from the main tube, fluidly couples the first pump 50 to a receptacle 68 that supplies the first pump 50 with a sterile solution of saline. A flexible length of tubing 69 is used for fluidly coupling the proximal end 70 of the main tube 66 to the receptacle 68. The end of the branch tube 67 is fluidly coupled to the first pump 50. A second pinch clamp 71 mounted on the outside of the tubing 69, operates as flow control valve to selectively control the flow of saline from the receptacle 68 to the first pump 50. A first one-way valve 72 fluidly couples the distal end 73 of the main tube 66 of the second tube element 65 to the branch tube 64 of the first tube element 60. The first one-way valve 72 allows fluid to flow only from the second tube element 65 to the first tube element 60.

The second pump 51 is fluidly coupled to the proximal end 75 of a second conventional inline rotary valve 74 having an air inlet 76. A second one-way valve 77 fluidly couples the distal If end 78 of the rotary valve 74 to the proximal end 63 of the main branch 61 of the first split tube element 60 (the distal end 62 of the main branch 61 of the first split tube element 60 is fluidly coupled to the catheter assembly 11). The second one-way valve 77 prevents air from being drawn back into the second pump 51 from the catheter assembly 11, as well as saline from pump 50. The air inlet 76 of the rotary valve 74 is provided with a conventional micro-pore air filter element 80 (typically a 0.2 micron air filter element) which is capable of filtering out bacteria. In a first position, the second rotary valve 74 permits outside air to be drawn only through the air inlet 76 and air filter element 80 into the second pump 51 for injection into the uterus and fallopian tubes. The air filter element 80 filters out bacteria from the air and thus, sterilizes the air drawn into the second pump 51. In a second position, the second rotary valve 74 permits the sterilized air drawn into the second pump 51 to be pumped through the second one-way valve 77 into the first split tube element 60 for injection into the into the uterus and fallopian tubes via the catheter assembly 11 as will be explained further on.

The apparatus 10 is typically operated by inserting the catheter 14 of the catheter assembly 11 into the vaginal canal so that the balloon 23 is positioned in the cervical canal or just past the cervical canal inside the uterine cavity of the uterus as explained in U.S. Pat. No. 5,624,399. The balloon is then inflated with saline using the catheter assembly syringe 33. The inflated balloon 23 locks the position of the apparatus 10 and seals the uterine cavity to prevent leakage of the saline therefrom so that imaging can then be performed on the subject uterus and/or fallopian tubes. The first pump 50 of the pump assembly 12 is operated to draw the sterile solution of saline from the receptacle 68 into the first pump 50. The second pinch clamp 71 is locked to pinch off the flexible tubing 69, thereby preventing the saline from being pump back into the receptacle 68 during operation of the first pump 50. The second pump 51 is operated with the second rotary valve 74 in the first position to draw microfiltered air into the second pump 51. The rotary valve 74 is then placed into the second position.

The physician uses a first hand to hold the pump assembly 12 and operate the first pump 50 to pump the saline through the first one-way valve 72, the first split tube element 60 and the second lumen 18 of the catheter 14. The pumped saline is injected, via the catheter 14 into the uterus and the fallopian tubes. The physician uses the second hand to operate an ultrasound scanner to sonographically observe the pathology of the uterus.

After ultrasonically observing the structures of the uterus using the saline, the physician operates the second pump 51 with the first hand. The second pump 51 pumps microfiltered air through the second rotary valve, the second one-way valve 77, the first split tube element 60 and into the second lumen 18 of the catheter 14 to mix air with the saline.

At this point, the mixture of saline and air is injected, via the catheter 14, into uterus and fallopian tubes by operating both pumps 50, 51 simultaneously with one hand by squeezing the syringe plungers and pump holder 52 together with one (the first) hand. The physician can then use the second hand to operate the ultrasound scanner again to sonographically observe the patency of the fallopian tubes.

Once ultrasonic imaging has been completed, the balloon 23 of the catheter assembly 11 is deflated and the catheter 14 of the apparatus 10 is withdrawn from the uterus through the cervical canal.

Figure 4:
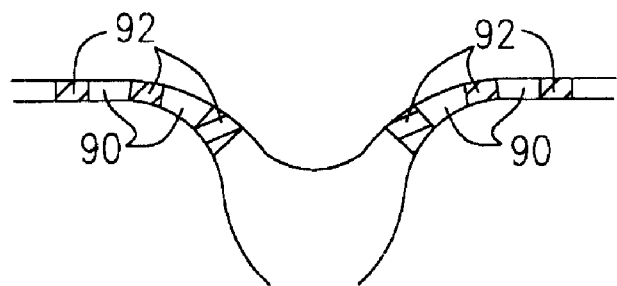
FIG. 4 is a sonographic view of a uterus depicting the visualization of the fallopian tubes according to the invention.

FIG. 4 depicts how the fallopian tubes are visualized according to the invention. The apparatus and method of the invention generates an alternating pattern of air bubbles 90 and saline 92 which can be seen in the unobstructed sections of the fallopian tubes.

While the foregoing invention has been described with reference to the above embodiment, various modifications and changes can be made without departing from the spirit of the invention. Accordingly, all such modifications and changes are considered to be within the scope of the appended claims.

What is claimed is:

1. An apparatus comprising:
   a pump assembly including first and second pumps, the pumps having independently operable actuators that allow independent operation of the pumps; and
   the first pump is adapted to inject a solution of sterile saline to a location in a body and the second pump is adapted to inject sterile air into the saline to generate air bubbles in the saline, wherein the saline solution and the air bubbles generated therein permit sonographic observation of the location and condition of the body.

2. The apparatus according to claim 1, wherein the pump assembly includes a pump holder that enables the first and second pumps of the pump assembly to be sequentially or simultaneously operable with one hand.

3. The apparatus according to claim 1, further comprising a tube element coupling the pump assembly to the catheter assembly.

4. The apparatus according to claim 1, wherein the desired location includes a human body.

5. The apparatus according to claim 1, wherein the desired location includes a uterus and its associated fallopian tubes.

6. The apparatus according to claim 1, wherein the first and second pumps include syringes.

7. The apparatus according to claim 1, wherein the catheter apparatus includes a balloon catheter.

8. The apparatus according to claim 1, wherein the catheter apparatus includes two lumens.

9. The apparatus according to claim 1, wherein the second pump includes a micro-pore filter for micro-filtering air drawn into the second pump.

10. The apparatus according to claim 1, wherein the first pump includes a reservoir that contains the solution of sterile saline.

11. A method for sonographically observing a location and condition of a body using an apparatus having a pump assembly and a catheter assembly fluidly coupled to the pump assembly, the pump assembly including a first pump for pumping a solution of sterile saline and a second pump for pumping micro-filtered air, the method comprising the steps of:
   inserting the catheter assembly into the location of the body;
   injecting the solution of sterile saline into the location of the body using the first pump of the pump assembly and the catheter assembly;
   injecting the micro-filtered air into the saline using the second pump of the pump assembly and the catheter assembly to generate air bubbles in the saline;
   injecting the saline with the air bubbles generated therein into the location of the body using the first and second pumps of the pump assembly and the catheter assembly; and
   ultrasonically imaging the location of the body to sonographically observe the location of the body using the bubbles generated in the saline.

12. The method according to claim 11, wherein prior to the micro-filtered air injecting step further comprising the step of ultrasonically imaging the location of the body to sonographically observe the condition of the body using the saline.

13. The method according to claim 11, wherein the injecting steps are manually performed using one hand.

14. The method according to claim 11, wherein the desired location includes a human body.

15. The method according to claim 11, wherein the desired location includes a uterus and its associated fallopian tubes.

16. The method according to claim 11, wherein the first and second pumps include syringes.

17. The method according to claim 11, wherein the catheter apparatus includes a balloon catheter.

18. The method according to claim 17, wherein the catheter apparatus includes two lumens.

19. The method according to claim 11, wherein the second pump includes a micro-air filter for micro-filtering air drawn into the second pump.

20. The method according to claim 11, wherein the first pump includes a reservoir that contains the solution of sterile saline.

21. A method for sonographically observing the uterus and its associated fallopian tubes using an apparatus having a pump assembly and a catheter assembly fluidly coupled to the pump assembly, the pump assembly including a first pump for pumping a solution of sterile saline and a second pump for pumping micro-filtered air, the method comprising the steps of:
   inserting the catheter assembly into the uterus;
   injecting the solution of sterile saline into the uterus using the first pump of the pump assembly and the catheter assembly;
   injecting the micro-filtered air into the saline using the second pump of the pump assembly and the catheter assembly to generate air bubbles in the saline;
   injecting the saline with the air bubbles generated therein into the uterus using the first and second pumps of the pump assembly and the catheter assembly; and
   ultrasonically imaging the uterus and fallopian tubes to sonographically observe the condition of the fallopian tubes using the bubbles generated in the saline.

* * * * *